United States Patent [19]

Heiss

[11] Patent Number: 4,585,875
[45] Date of Patent: Apr. 29, 1986

[54] PROCESS FOR PREPARING 4,4-BIS-BENZ-OX(-THI,-IMID)-AZOL-2-YL-STILBENES

[75] Inventor: Lorenz Heiss, Hofheim am Taunus, Fed. Rep. of Germany

[73] Assignee: Hoechst Aktiengesellschaft, Fed. Rep. of Germany

[21] Appl. No.: 580,865

[22] Filed: Feb. 16, 1984

[30] Foreign Application Priority Data

Feb. 18, 1983 [DE] Fed. Rep. of Germany ....... 3305578

[51] Int. Cl.$^4$ ................. C07D 277/62; C07D 263/62; C07D 235/04
[52] U.S. Cl. ..................................... 548/156; 548/219; 548/328
[58] Field of Search .................. 548/219, 156, 328

[56] References Cited

U.S. PATENT DOCUMENTS

| 4,156,778 | 5/1979 | Rösner et al. | 544/296 |
| 4,282,355 | 8/1981 | Erckel et al. | 548/217 |

FOREIGN PATENT DOCUMENTS

| 0093444 | 11/1983 | European Pat. Off. | 548/219 |
| 1026368 | 4/1966 | United Kingdom | 548/219 |
| 721429 | 3/1980 | U.S.S.R. | 548/219 |

OTHER PUBLICATIONS

Vernigor et al., *Chem. Heterocyc. Compounds*, 17:328–332 (1981).
Khim. Geterotsik. Soedin. 1981, pp. 463–467 (Vernigor et al.).

Primary Examiner—George F. Lesmes
Assistant Examiner—S. A. Gibson
Attorney, Agent, or Firm—Connolly and Hutz

[57] ABSTRACT

A process for preparing 4,4′-bis-benz-ox(-thi,-imid)-azol-2-yl-stilbenes of the formula

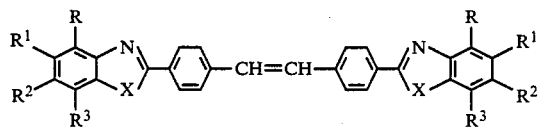

wherein R, $R^1$, $R^2$ and $R^3$ may be the same or different from each other and denote hydrogen, $C_1$–$C_4$-alkyl, $C_1$–$C_4$-alkoxy, $C_1$–$C_4$-alkoxycarbonyl, chlorine, bromine, nitro or sulfo and X denotes oxygen, sulfur or NH, which comprises reacting a (4-chloromethyl)-iminobenzoic acid alkyl ester of the formula

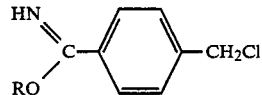

wherein R denotes $C_1$–$C_4$-alkyl or $C_1$–$C_4$-alkoxyethyl, or HCl salts thereof, with o-aminophenol, o-aminothiophenol or o-phenylene diamine and reacting the resulting 2-benz-ox(-thi,-imid)-azolyl-4-chloromethyl-benzenes with potassium hydroxide or sodium hydroxide in a polar aprotic solvent.

1 Claim, No Drawings

PROCESS FOR PREPARING 4,4-BIS-BENZ-OX(-THI,-IMID)-AZOL-2-YL-STILBENES

It is known from Khim. Geterotsilkl. Soedin 1981, page 464 that the reaction of bromomethylbenzoxazol-2-yl-benzene with the fourfold quantity of potassium hydroxide in dimethyl formamide gives 4,4'-bis-(benzoxazol-2-yl)-dibenzyl ether in a yield of 51%. It has now been surprisingly found that this reaction proceeds in a quite different manner and that it results in bis-benzoxazolstilbenes which are very important optical brighteners, if the chloromethyl compound is used instead of the bromomethyl compound as the starting compound.

Subject of the present invention is, consequently, a process for preparing 4,4'-bis-benz-ox(-thi,-imid)-azol-2-yl-stilbenes of the formula

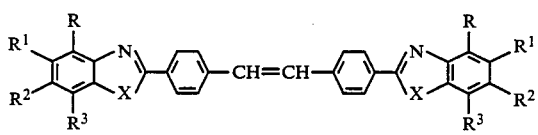

wherein R, $R^1$, $R^2$ and $R^3$ are the same or different from each other and denote hydrogen, $C_1$–$C_4$-alkyl, $C_1$–$C_4$-alkoxy, $C_1$–$C_4$-alkoxycarbonyl, chlorine, bromine, nitro or sulfo and X denotes oxygen, sulfur or NH, which comprises reacting a (4-methyl)-iminobenzoic acid alkyl ester of the formula

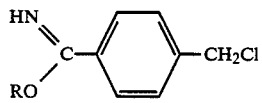

wherein R denotes $C_1$–$C_4$-alkyl or $C_1$–$C_4$-alkoxyethyl, or salts thereof, with o-aminophenol, o-aminothiophenol or o-phenylene diamine followed by a reaction of the resulting 2-benz-ox(-thi,-imid)-azolyl-4-chloromethyl-benzenes with potassium hydroxide or sodium hydroxide in a polar aprotic solvent.

(4-Chloromethyl)-iminobenzoic acid alkyl ester used as the starting compound is prepared by dispersing p-cyanobenzyl chloride in an excess of the alcohol of the formula R-OH and introducing subsequently hydrogen chloride, whereby the HCl salts of the imino esters of the above formula are obtained.

The resulting salts are reacted with o-aminophenol, o-aminothiophenol or o-phenylene diamine by heating in an inert organic solvent, preferably a lower alcohol, at a temperature ranging from room temperature to the boiling temperature of the solvent used. Upon completion of the reaction, water is added, the reaction product is suction-filtered and the filtrate is washed with water. The 2-benzoxazolyl-4-chloromethylbenzene or the corresponding benzthiazolyl- or benzimidazolyl compounds are thus obtained.

To prepare the stilbene compounds, the chloromethylbenzene compounds obtained are dissolved in an anhydrous aprotic polar solvent, preferably dimethyl formamide, and brought to dimerize by adding powdery sodium hydroxide or potassium hydroxide. The quantity of alkali hydroxide should be about 2 to 4 mols, referred to one mol of the chloromethyl compound. The alkali hydroxide is used in a powdery form to permit a smooth course of the reaction. The reaction takes place at room temperature, until the whole quantity of organically bound chlorine has reacted. To bind the water formed by the neutralization step, the addition of compounds such as, for example, $Na_2O$, CaO, NgO or NaOH may be advantageous. The yield is thus increased.

In general, the reaction time ranges from 6 to 12 hours. At the end of the reaction, the reaction mixture is acidified using an acid, preferably an anhydrous organic acid such as glacial acetic acid. For the further treatment, the reaction mixture is heated to the boil in order to dissolve by products, followed by suction-filtration in the hot state. The filtrate is washed with solvents and with water until chloride ions can no longer be detected in the washing water. The analytically pure stilbene compound is obtained upon drying in a yield of about 90%.

These stilbene compounds of the formula specified at the beginning are suitable for use as optical brighteners. They can be prepared in a high yield in economic manner by the above-described process.

The following example serve to illustrate the invention:

EXAMPLE 75.8 g (0.5 mol) of p-cyanobenzyl chloride are dispersed in 32 g (1 mol) of methanol and about 35.5 g (1 mol) of hydrogen chloride are introduced at 5°–10° C. The reaction mixture is stirred for about 20 hours, until the nitril band in the infrared spectrum at 2220 $cm^{-1}$ has disappeared. 110 g (0.5 mol) of 4-chloromethyl-benzimidomethyl ether hydrochloride are obtained after having removed methanol and hydrogen. Yield: quantitative.

| Analysis: | C % | H % | Cl % | $Cl^-$ % |
|---|---|---|---|---|
| found: | 49.0 | 5.0 | 32.0 | 16.1 |
| calculated: | 49.2 | 5.0 | 32.2 | 16.1. |

110 g (0.6 moles) 4-chloromethyl-iminobenzoic acid methyl ester hydrochloride were dispersed in 500 g methanol and 54,5 g (0,5 moles) of of o-aminophenol in 120 g glacial acetic acid were added. The reaction mixture was refluxed at 65° C. for one hour, suction-filtered, washed with 30 g methanol and then with water until the washing water was free from chlorine ions. Upon drying 117 g (0,48 moles) of 4-chloromethyl-benzoxazol-2-yl-benzene were obtained in a yield of 96% of the the theory. Melting point: 149° C.

| Analysis | C % | H % | Cl % |
|---|---|---|---|
| found | 69,0 | 4,1 | 14,6 |
| calculated | 99,1 | 4,1 | 14,6 |

16 g (0.4 mol) of sodium hydroxide powder are dispersed while stirring in 150 g of dimethyl formamide under nitrogen, 24.4 g (0.1 mol) of 4-chloromethylbenzoxazol-2-yl-benzene are introduced and the reaction mixture is stirred for about 6–12 hours until the whole quantity of organically bound chlorine has reacted.

The product is acidified with acetic acid, heated to the reflux, suction-filtered at a temperature below 100° C., washed with dimethyl formamide and, subsequently, with water, until the washing water is free of chlorine ions and the product is dried. Greenish-yellow fluorescent crystals of 4,4'-bisbenzoxazol-2-yl-stilbenes are obtained in a yield of 18.6 g (89.8% of the theory). Melting point: 355°–360° C.

| Analysis: | C % | H % | N % |
|---|---|---|---|
| found: | 80.8 | 4.3 | 6.8 |
| calculated: | 81.1 | 4.3 | 6.8. |

The final products listed in the following table are obtained when working under the same reaction conditions.

TABLE 1

| Ex. | Starting products | Final products | Melting point | C, H, Cl-Analysis | Yield |
|---|---|---|---|---|---|
| (2) | 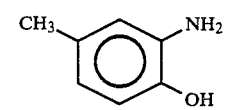 | 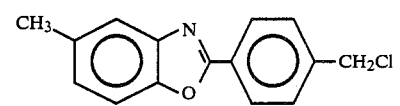 | 144° C. | found: 69.7%; 4.8%; 13.5%<br>calc.: 69.9%; 4.7%; 13.8% | 91% |
| (3) | 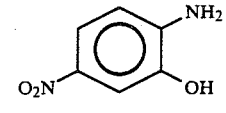 | 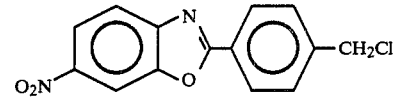 | 138° C. | found: 58.1%; 3.3%; 11.9%<br>calc.: 58.2%; 3.1%; 12.2% | 88% |
| (4) | 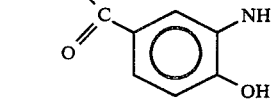 | 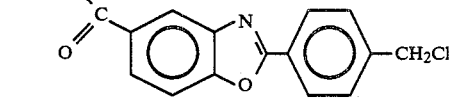 | 137° C. | found: 64.6%; 4.4%; 11.0%<br>calc.: 64.8%; 4.4%; 11.3% | 82% |
| (5) | 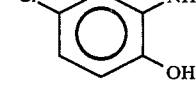 | 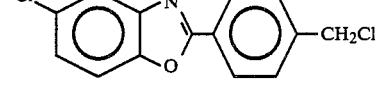 | 167° C. | found: 60.0%; 3.3%; 24.9%<br>calc.: 60.3%; 3.2%; 25.5% | 86% |
| (6) | 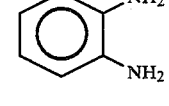 | 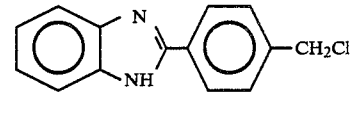 | subl. 200° C. | found: 68.9%; 4.8%; 14.2%<br>calc.: 69.2%; 4.6%; 14.6% | 90% |
| (7) | 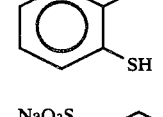 | 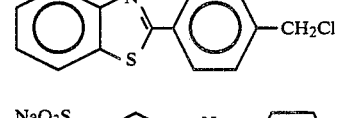 | 114° C. | found: 64.3%; 3.8%; 13.5%<br>calc.: 64.9%; 3.9%; 13.7% | 56% |
| (8) | 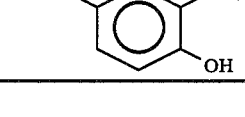 | 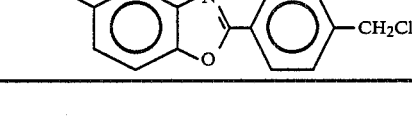 | — | found: 48.3%; 2.7%; 10.2%<br>calc.: 48.7%; 2.6%; 10.2% | 51% |

TABLE 2

| Ex. | Starting products | Final products | Melt. point | C, H, N-Analysis | Yield |
|---|---|---|---|---|---|
| (2) | 4-CH₃-phenyl-benzoxazole with CH₂Cl | stilbene-linked bis-benzoxazole with CH₃ groups | 280–285° C. | found: 80.8%; 5.1%; 6.2%<br>calc.: 81.2%; 5.2%; 6.3% | 94% |
| (3) | ethyl ester benzoxazole-CH₂Cl | bis-benzoxazole stilbene with OC₂H₅ ester | 272–278° C. | found: 72.8%; 4.8%; 5.1%<br>calc.: 73.1%; 4.7%; 5.0% | 88% |
| (4) | 5-Cl-benzoxazole-CH₂Cl | Cl-substituted stilbene bis-benzoxazole | 306–310° C. | found: 69.1%; 3.3%; 5.7%<br>calc.: 69.6%; 3.3%; 5.8% | 91% |
| (5) | benzimidazole-CH₂Cl | stilbene bis-benzimidazole | >340° C. dec. | found: 81.2%; 4.7%; 13.5%<br>calc.: 81.6%; 4.8%; 13.6% | 86% |
| (6) | benzothiazole-CH₂Cl | stilbene bis-benzothiazole | 302–308° C. | found: 75.0%; 4.1%; 3.1%<br>calc.: 75.3%; 4.0%; 3.1% | 72% |
| (7) | Na⊕ ⊖O₃S-benzoxazole-CH₂Cl | sulfonated stilbene bis-benzoxazole (Na⊕ SO₃⊖) | >360° C. | found: 53.9%; 2.5%; 4.4%<br>calc.: 54.4%; 2.6%; 4.5% | 76% |
| (8) | benzoxazole-CH₂Br | stilbene bis-benzoxazole | 358–362° C. | found: 80.7%; 4.3%; 6.7%<br>calc.: 81.1%; 4.3%; 6.8% | 90% |

What is claimed is:

1. A process for preparing 4,4'-bis-benz-ox(-thi,-imid)-azol-2-yl-stilbenes of the formula

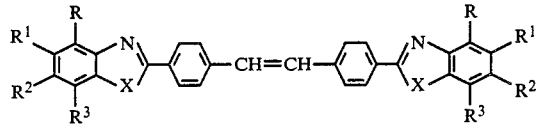

wherein R, $R^1$, $R^2$ and $R^3$ may be the same or different from each other and denote hydrogen, $C_1$–$C_4$-alkyl, $C_1$–$C_4$-alkoxy, $C_1$–$C_4$-alkoxycarbonyl, chlorine, bromine, nitro or sulfo and X denotes oxygen, sulfur or NH, which comprises reacting a (4-chloromethyl)-iminobenzoic acid alkyl ester of the formula

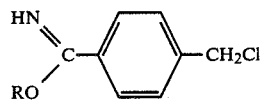

wherein R denotes $C_1$–$C_4$-alkyl or $C_1$–$C_4$-alkoxyethyl, or HCl salts thereof, with o-aminophenol, o-aminothiophenol or o-phenylene diamine and reacting the resulting 2-benzox(-thi,-imid)-azolyl-4-chloromethyl-benzenes with potassium hydroxide or sodium hydroxide in a polar aprotic solvent.

* * * * *

UNITED STATES PATENT AND TRADEMARK OFFICE
CERTIFICATE OF CORRECTION

PATENT NO. : 4,585,875
DATED : April 29, 1986
INVENTOR(S) : Lorenz Heiss

It is certified that error appears in the above-identified patent and that said Letters Patent is hereby corrected as shown below:

The term of this patent subsequent to April 2, 2002 has been disclaimed.

Signed and Sealed this

Eighth Day of July 1986

[SEAL]

*Attest:*

DONALD J. QUIGG

*Attesting Officer*  *Commissioner of Patents and Trademarks*